(12) United States Patent
Bystryak et al.

(10) Patent No.: US 9,023,028 B2
(45) Date of Patent: *May 5, 2015

(54) ELECTROSURGICAL DEVICE WITH CONTROLLABLE ELECTRIC FIELD PROFILE

(71) Applicant: Smith & Nephew, Inc., Memphis, TN (US)

(72) Inventors: Ilya Bystryak, Salem, MA (US); Lim Cheung, Concord, MA (US)

(73) Assignee: Smith & Nephew, Inc., Memphis, TN (US)

( * ) Notice: Subject to any disclaimer, the term of this patent is extended or adjusted under 35 U.S.C. 154(b) by 99 days.

This patent is subject to a terminal disclaimer.

(21) Appl. No.: 13/957,032

(22) Filed: Aug. 1, 2013

(65) Prior Publication Data

US 2013/0331834 A1    Dec. 12, 2013

Related U.S. Application Data

(63) Continuation of application No. 13/749,226, filed on Jan. 24, 2013, now Pat. No. 8,500,729, which is a continuation of application No. 12/607,563, filed on Oct. 28, 2009, now Pat. No. 8,388,615.

(60) Provisional application No. 61/109,125, filed on Oct. 28, 2008.

(51) Int. Cl.
*A61B 18/14* (2006.01)
*A61B 18/18* (2006.01)
*A61B 18/12* (2006.01)
*A61B 18/00* (2006.01)

(52) U.S. Cl.
CPC ............. *A61B 18/18* (2013.01); *A61B 18/1206* (2013.01); *A61B 18/1492* (2013.01); *A61B 2018/0016* (2013.01); *A61B 2018/00577* (2013.01); *A61B 2018/00738* (2013.01); *A61B 2018/0075* (2013.01); *A61B 2018/00779* (2013.01); *A61B 2018/00869* (2013.01); *A61B 18/00* (2013.01)

(58) Field of Classification Search
CPC .... A61B 18/00; A61B 18/18; A61B 18/1206; A61B 18/1492; A61B 2018/0016; A61B 2018/00577; A61B 2018/00738; A61B 2018/0075; A61B 2018/00779; A61B 2018/00869

See application file for complete search history.

(56) References Cited

U.S. PATENT DOCUMENTS

2002/0161361 A1*  10/2002  Sherman et al. ............... 606/34
2009/0318915 A1*  12/2009  Hosier et al. .................. 606/33

* cited by examiner

*Primary Examiner* — Michael Peffley
*Assistant Examiner* — Daniel Fowler
(74) *Attorney, Agent, or Firm* — Chapin IP Law, LLC

(57) ABSTRACT

An electrosurgical device includes a plurality of electrodes arranged to form a tissue treatment surface and a power supply. The power supply is configured to deliver a first drive signal with a first phase to at least a first one of the plurality of electrodes and a second drive signal with a second phase to at least a second one of the plurality of electrodes such that an electric field extends from the tissue treatment surface, where the first phase and the second phase are different. The power supply is further configured to receive an input from an operator of the electrosurgical device, and adjust the first phase or the second phase such that an aspect of the electric field extending from the tissue treatment surface changes in response to the input from the operator.

20 Claims, 10 Drawing Sheets

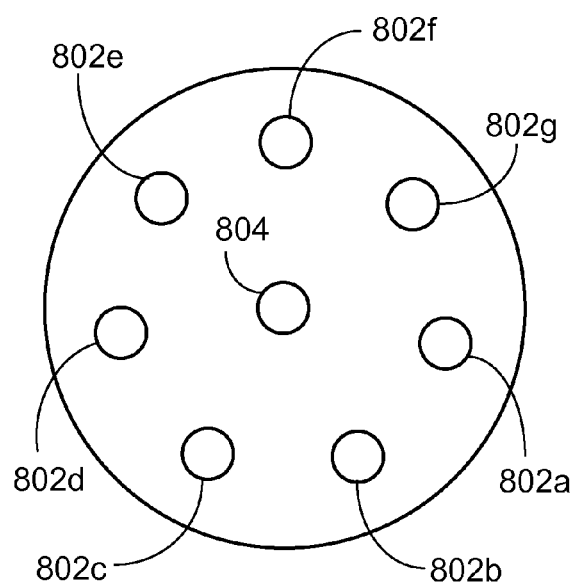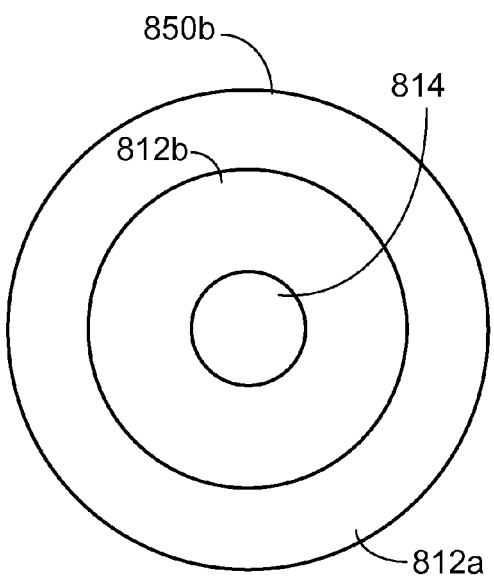
FIG. 8A    FIG. 8B
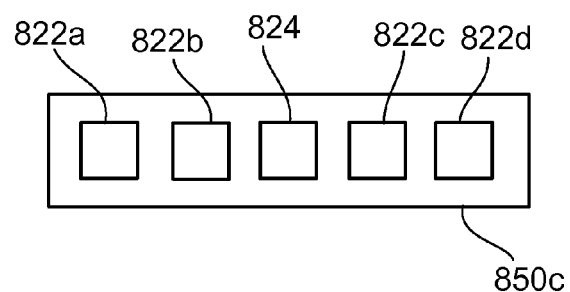
FIG. 8C

ELECTROSURGICAL DEVICE WITH CONTROLLABLE ELECTRIC FIELD PROFILE

CROSS-REFERENCE TO RELATED APPLICATIONS

This application is a continuation of U.S. patent application Ser. No. 13/749,226, filed Jan. 24, 2013, now U.S. Pat. No. 8,500,729, which is a continuation of U.S. patent application Ser. No. 12/607,563, filed Oct. 28, 2009, now U.S. Pat. No. 8,388,615, which claims priority from U.S. Provisional Application Ser. No. 61/109,125, filed Oct. 28, 2008. The contents of U.S. patent application Ser. No. 12/607,563 and U.S. Provisional Application Ser. No. 61/109,125 are incorporated herein by reference in their entirety.

TECHNICAL FIELD

This description relates to an electrosurgical device with a controllable electric field profile.

BACKGROUND

Surgical instruments employing RF energy for treatment are used in a variety of surgical procedures. Such instruments generally include an RF probe that delivers RF energy to the part of the body to be affected by the electrosurgical procedure.

RF probes can be mono-polar or bi-polar. Mono-polar probes have a single RF electrode. The RF energy of the mono-polar probe passes from the RF electrode through the area to be treated and then to a return electrode attached to the body, often a foot or more away from the RF electrode. Bipolar probes include two terminals, an active electrode and a return electrode, which can both be positioned within the patient at the area to be treated.

SUMMARY

In one aspect, an electrosurgical device includes a plurality of electrodes arranged to form a tissue treatment surface and a power supply. The power supply is configured to deliver a first drive signal with a first phase to at least a first one of the plurality of electrodes and a second drive signal with a second phase to at least a second one of the plurality of electrodes such that an electric field extends from the tissue treatment surface, where the first phase and the second phase are different. The power supply is further configured to receive an input from an operator of the electrosurgical device, and adjust the first phase or the second phase such that an aspect of the electric field extending from the tissue treatment surface changes in response to the input from the operator.

Implementations of any aspect may include one or more of the following features. The power supply may include a power factor correction and rectifier module configured to convert an AC power signal to a DC power signal, and a phase shifting module configured to generate a plurality of phase-shifted power signals. The power supply may be configured to deliver the first drive signal and the second drive signal such that a plasma is formed in front of the tissue treatment surface. The shape of a plasma may change when the aspect of the electrical field extending from the tissue treatment surface changes.

The plurality of electrodes may include the first one of the plurality of electrodes, the second one of the plurality of electrodes, and a third electrode being coupled to ground.

The plurality of electrodes may include a first pair of electrodes and a second pair of electrodes, where the first pair of electrodes includes the first one of the plurality of electrodes and a third electrode, and the second pair of electrodes includes the second one of the plurality of electrodes and a fourth electrode. The power supply may be configured to deliver the first drive signal to the third electrode 180 degrees out of phase with respect to the first phase and to deliver the second drive signal to the fourth electrode 180 degrees out of phase with respect to the second phase. The first drive signal and the second drive signal may be RF drive signals with a frequency greater than 3 MHz, and a ground pad may be coupled to ground and may be configured to be coupled to a patient's body during use.

The aspect of the electrical field may be a shape and/or intensity of the electrical field.

In another aspect, a method for performing electrosurgery with an electrosurgical device includes delivering a first drive signal with a first phase to at least a first electrode and a second drive signal with a second phase to at least a second electrode such that an electric field extends from the tissue treatment surface, where the first phase and second phase are different. The method further includes receiving an input from an operator of the electrosurgical device, and adjusting the first phase or the second phase such than an aspect of the electric field extending from the tissue treatment surface changes in response to the input from the operator.

Implementations of any aspect may include one or more of the following features. Performing electrosurgery may include grounding a third electrode. The aspect of the electrical field may be a shape and/or intensity of the electrical field.

The method may include delivering the first drive signal to a third electrode 180 degrees out of phase with respect to the first phase, and delivering the second drive signal to a fourth electrode 180 degrees out of phase with respect to the second phase. Delivering the first drive signal and the second drive signal may include delivering RF drive signals with a frequency greater than 3 MHz. Performing electrosurgery also may include grounding a ground pad, and coupling the ground pad to a patient's body.

Delivering the first drive signal and the second drive signal may include delivering the first drive signal and the second drive signal such that a plasma is formed in front of the tissue treatment surface. A shape of the plasma may change when the aspect of the electrical field extending from the tissue treatment surface changes.

The details of one or more implementations are set forth in the accompanying drawings and the description below. Other features, objects, and advantages will be apparent from the description and drawings, and from the claims.

DESCRIPTION OF DRAWINGS

FIGS. 8A to 8C are top views of the distal portion of electrosurgical device showing various electrode layouts.

DETAILED DESCRIPTION

Figure 1:
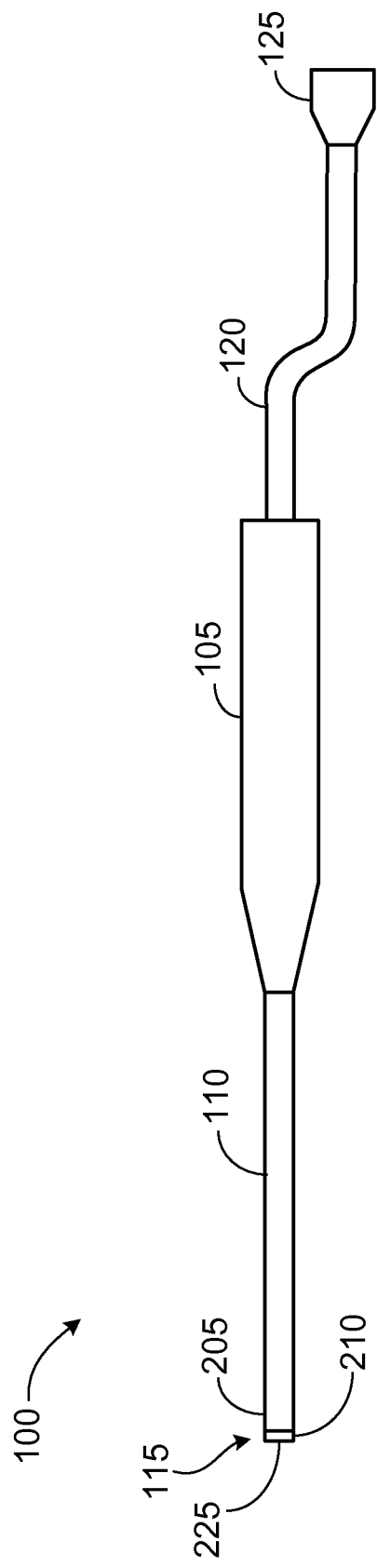
FIG. 1 is a side view of an electrosurgical device.

Referring to FIG. 1, an electrosurgical device 100 includes a handle 105 connected to an elongated shaft 110 and a power cable 120. Power cable 120 includes a power connector 125 for connection to a source of electrical energy such as an RF power generator (not shown). Shaft 110 is hollow and formed from, for example, an insulative plastic such as Teflon, polyethylene, polystyrene, or other thermally molded plastic, or made from a metal tube. In general, the device 100 is sized and shaped for endoscopic surgical procedures. Such procedures may include, for example, ablation, cutting, or coagulation.

Shaft 110 has a distal portion 115 that includes an insulated region 205 terminating at a disc 210, which includes embedded electrodes 230a-230e (FIG. 2A) and a treatment surface 225. Applying RF signals to one or more of the electrodes 230a-230e generates an electric field that extends from the tissue treatment surface. As described further below, an operator may use an input on, for example, the RF generator to indicate a desired shape and/or intensity of the electric field. As a result of the operator input, the phase, amplitude, and/or frequency of one or more of the signals applied to the electrodes 230a-230e are changed to achieve the desired shape and/or intensity.

Disc 210 is, for example, approximately 5 mm in diameter and has an overall thickness of between about 25 and 60 mils. Disc 210 is formed from an insulative material that preferably has high electrical isolation to limit voltage breakdown between adjacent electrodes, and is preferably resistant to high temperature and the aggressive chemical environment of RF plasmas.

Figure 2A:
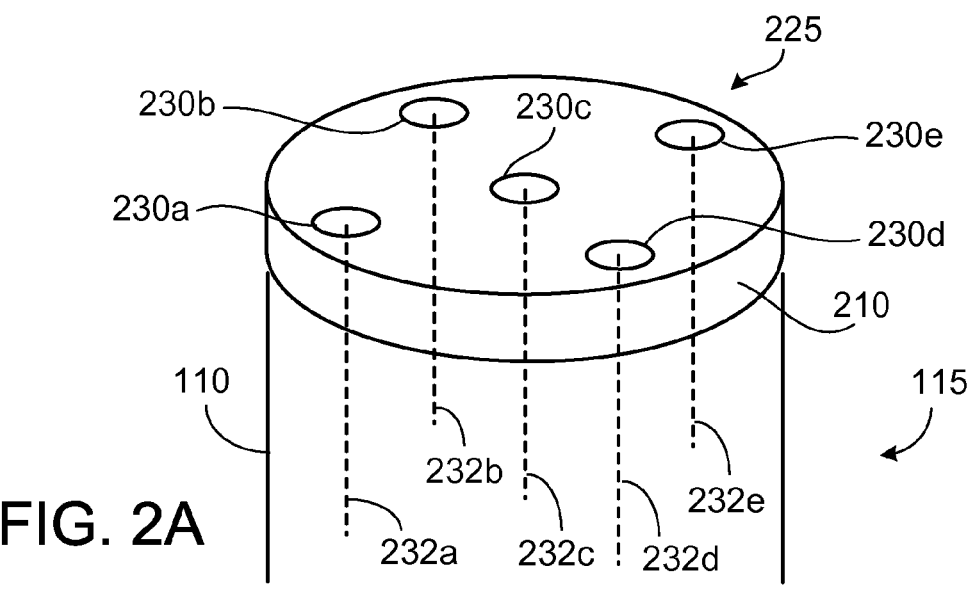
FIG. 2A is a perspective view of a distal portion of the electrosurgical device.
Figure 2B:
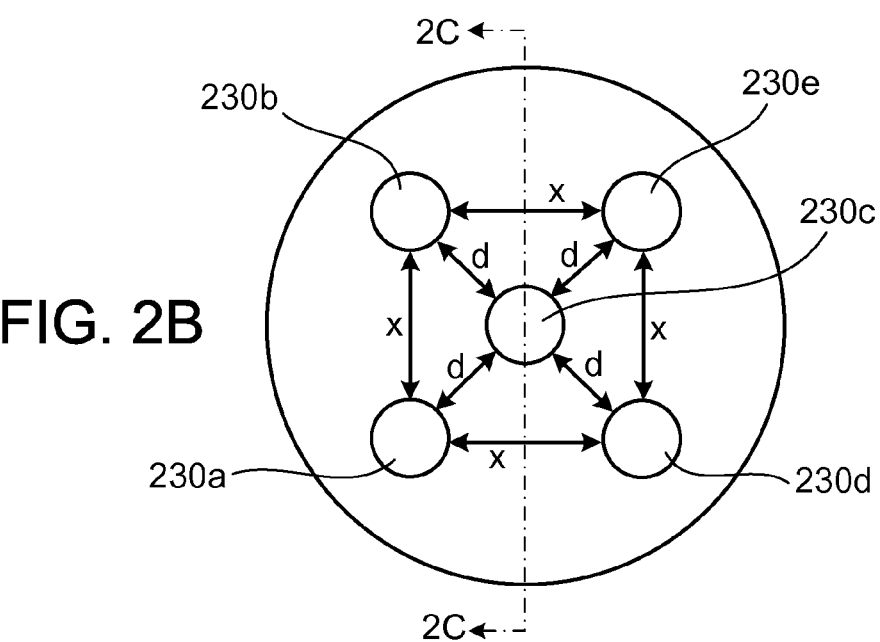
FIG. 2B is a plan view of the distal portion of the electrosurgical device.
Figure 2C:
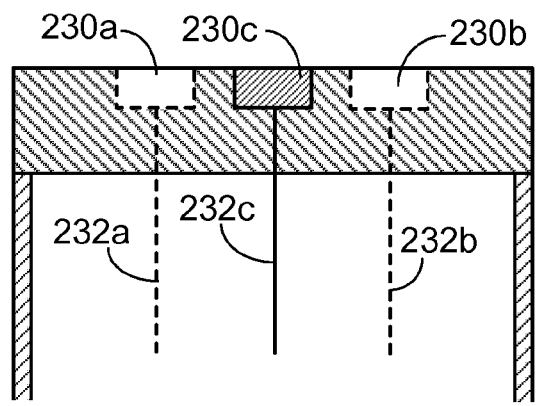
FIG. 2C is a cross-sectional view of the distal portion of the electrosurgical device taken along the line 2C-2C in FIG. 2B.

Referring to FIGS. 2A-2C, embedded electrodes 230a to 230e are exposed at the tissue treatment surface 225, such that the material of disc 210 does not cover the electrodes 230a to 230e. Electrodes 230a to 230e are adjacent to one another such that electrode 230c is at the center of disc 210 and electrodes 230a, 230b, 230d, and 230e surround electrode 230c. Electrodes 230a, 230b, 230d, and 230e are equally separated from electrode 230c by a distance d, and equally separated from one another by a distance x to form a square around electrode 230c. Electrodes 230a to 230e may be, for example, on the order of 10 millimeters in diameter and the distances d and x may be between, for example, 1 to 10 millimeters. The distance d may be equal to or different from the distance x.

As shown in FIGS. 2A, 2B, 2C, and 3A, electrode 230a is connected to a first lead 232a that connects electrode 230a to a first terminal 330a (FIG. 3A) of the RF power generator 310 through power cable 120 and connector 125. Similarly, electrodes 230b-e are connected to leads 232b-e, respectively, that connect the electrodes to respective terminals 330b-e (FIG. 3A) of the RF power generator 310. Leads 232a-e pass through the hollow portion of shaft 110 to power cable 120. Leads 232a, 232b, 232d, and 232e are supplied with RF signals having different phases by an RF power generator 310 though terminals 330a, 330b, 330d, and 330e, respectively. Lead 232c is connected to the ground terminal 330c of the RF power generator 310. The RF signals supplied to the electrodes 230a, 230b, 230d, and 230e result in an electric field extending from the tissue treatment surface 225 and in currents between the electrodes 230a to 230e. The shape and intensity of the electric field will change based on the phases and voltage magnitudes of the RF signals, as described below. Therefore, based on an operator input 320 specifying a desired shape and/or intensity of an electric field for a surgery being performed, the RF power generator 310 generates appropriate RF signals with different phases and/or voltage magnitudes to be applied to terminals 330a, 330b, 330d, and 330e.

Figure 3A:
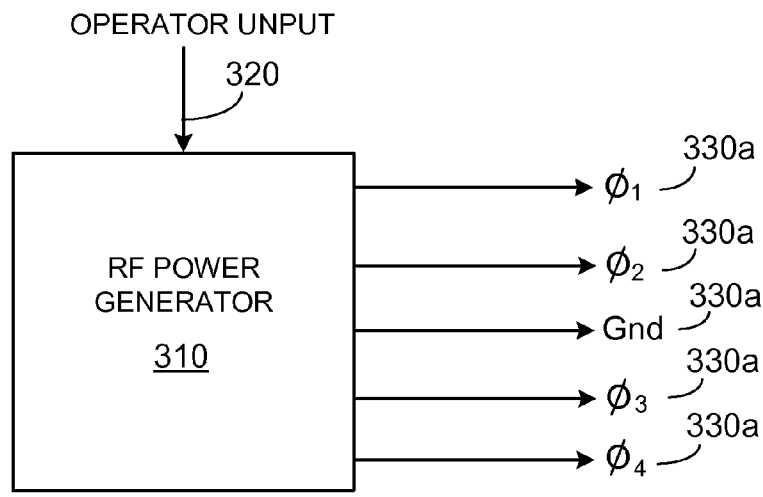
FIG. 3A is a schematic showing the inputs to and outputs from a RF power generator.
Figure 3B:
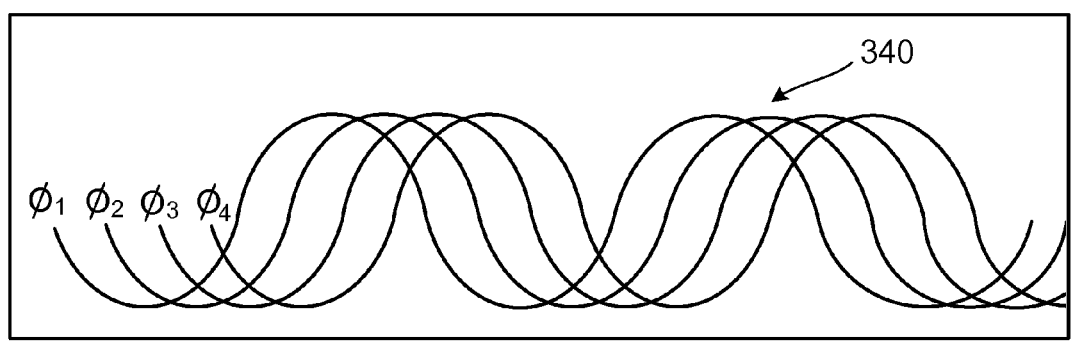
FIG. 3B is a diagram showing an example of RF signals generated by the RF power generator.

Referring to FIG. 3B, an example of the RF signals 340 applied to terminals 330a, 330b, 330d, and 330e over time is illustrated. In the example illustrated, the magnitudes of the RF signals applied to terminals 330a, 330b, 330d, and 330e are equal, but the phases of the RF signals are each different. Specifically, in the example shown in FIG. 3B, the RF signals applied to terminals 330a, 330b, 330d, and 330e are 360 degrees divided by the number of non-ground electrodes (for example, 90 degrees) out of phase.

The RF signals 340 applied to terminals 330a, 330b, 330d, and 330e are sinusoidal. However, other types of signals can be used, such as square waves or triangle waves. Additionally, to achieve the desired shape and/or intensity of the electric field, the voltage magnitudes of the RF signals applied to terminals 330a, 330b, 330d, and 330e may also be adjusted.

Figure 4A:
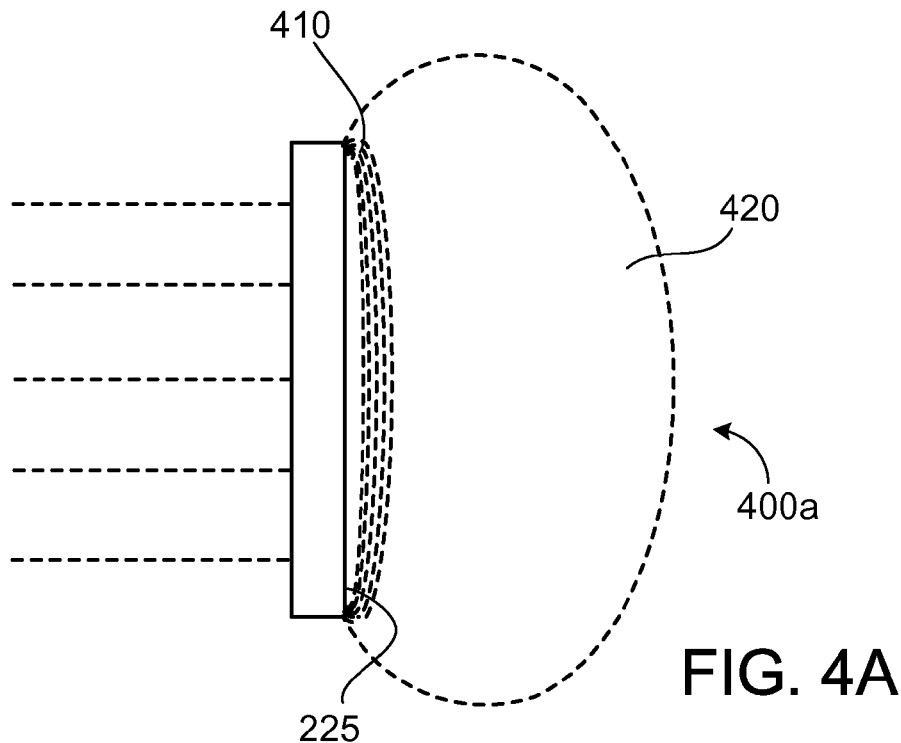
FIGS. 4A and 4B are diagrams showing examples of electric fields extending from the distal portion of the electrosurgical device.

The profile of an electric field resulting from RF signals applied to electrodes depends on several variables, such as the number of electrodes, the configuration of electrodes, and phase difference between the RF signals. For example, in some configurations, a substantially uniform electric field is generated if the phase difference between the RF signals is 360 degrees divided by the number of non-ground electrodes, as illustrated in FIG. 4A. The exact field profile for a given configuration and phase difference can be determined by simulation using, for example, finite element analysis.

Referring again to FIG. 4A, in some instances, equal phase differences between the electrodes 230a, 230b, 230d, and 230e can result in an electric field 400a that extends from and is substantially uniform across the tissue treatment surface 225 at a given distance from the tissue treatment surface 225. The substantially uniform electric field may be generated, for example, by the signals illustrated in FIG. 3B. The magnitude of the intensity of the substantially uniform electric field at a given distance from the tissue treatment surface 225 is proportional to:

$$\frac{1}{r^x}$$

where x is equal to the number of non-ground electrodes embedded within disc 210 and r is equal to the distance from the tissue treatment surface 225.

The electric field 400a includes a near field 410 and a far field 420. The dashed lines in the near and far fields 410 and 420 represent equipotential lines of the electric fields. Near field 410 is stronger than far field 420 because of its proximity to the electrodes 230a to 230e exposed at the tissue treatment surface 225.

Figure 4B:
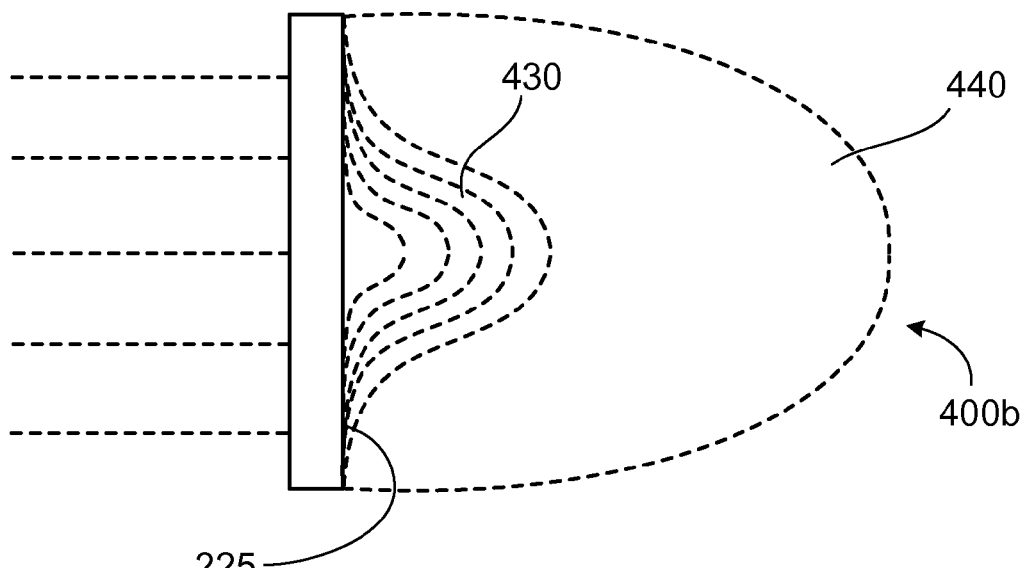

Referring to FIG. 4B, the intensity profile of the an electric field can be changed by changing the phase differences between the RF signals applied to terminals 330a, 330b, 330d, and 330e. For example, if the operator desires a more narrow intensity profile of the electric field, the operator can use the operator input 320 on the RF power generator 310 to indicate the more narrow field profile. As a result, the RF power generator 310 changes the phase differences such that the electric field is more narrowly focused, which is illustrated by field 400b in FIG. 4B. Electric field 400b includes a near field 430 and a far field 440. Near field 430 is stronger than far field 440 because of its proximity to the electrodes 230a to 230e exposed at the tissue treatment surface 225. The intensity of electric fields 410 to 440 may be increased or decreased by increasing or decreasing the magnitudes of the RF signals, respectively.

In one example, a touch screen can be used as an operator input device. The touch screen shows a representation of the near field extending from the tissue treatment surface. The operator can manipulate points along the near field curve to show a desired near field profile. The RF power generator 310 then changes the phases and/or magnitudes of the RF signals so that the electric field generated has the desired near field profile.

Different intensities of electric fields can be used for various treatments. For example, a high density electric field can ignite a plasma discharge for use in ablating or cutting tissue. For instance, in some environments, a high density electric field up to about 200 V/mil (which is equal to 7.9 kV/mm) can be used to ignite a plasma. The particular density needed to ignite a plasma for a given environment and configuration can be determined through routine experimentation or simulation. The electric field intensity profile will control the shape of the plasma discharge. For example, the shape of a plasma ignited based on the substantially uniform electric field shown in FIG. 4A will also be substantially uniform across the tissue treatment surface 225, such as the plasma 615 illustrated in FIG. 6. In another example, the shape of a plasma ignited based on the more narrow electric field intensity profile shown in FIG. 4B will correspondingly be more narrow.

In a procedure such as coagulation, on the other hand, the energy density of an electric field is kept low enough to prevent the ignition of a plasma discharge. Coagulation is performed using thermal treatment with a RF current density of up to, for example, about 0.8 A/mm squared. Similarly, an electric field with a low power density can be used to kill cells in a treatment area.

Different electric field intensity profiles can also be used for various treatments. For example, to treat a large surface area, a broad electric field profile, such as the substantially uniform electric field shown in FIG. 4A can be used. To more specifically target unhealthy tissue or to coagulate a small artery, on the other hand, a more narrow electric field profile can be used.

Figure 5:
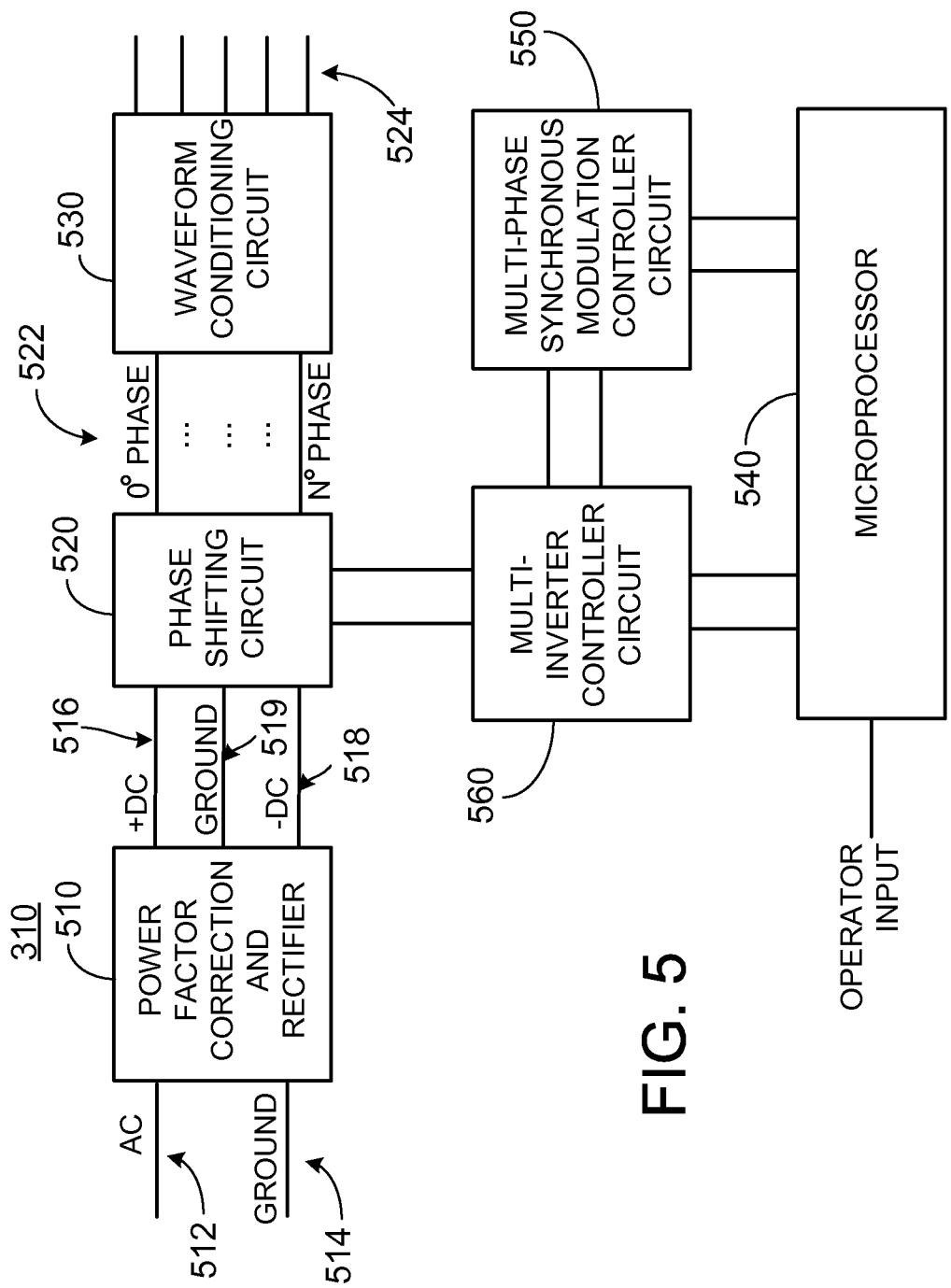
FIG. 5 is a schematic of an example of the RF power generator.

Referring to FIG. 5, one embodiment of the RF power generator 310 includes a power factor correction and rectifier circuit 510, a phase shifting circuit 520, a waveform conditioning circuit 530, a microprocessor 540, a multi-phase synchronous modulation controller circuit 550, and a multi inverter controller circuit 560.

The power factor correction and rectifier circuit 510 receives an alternating current (AC) power signal 512 and a ground signal 514. The power factor correction and rectifier circuit 510 performs power factor correction so that the load, i.e. resistance, of the power factor correction and rectifier circuit 510 is linear. As such, the current on the AC power signal 512 follows the voltage of the AC power signal 512. The power factor correction and rectifier circuit 510 also rectifies the AC power signal 512 to generate a positive direct current (DC) power signal 516 and a negative DC power signal 518. The ground signal 514 is also output by the power factor correction and rectifier circuit 510 as ground signal 519.

The phase shifting circuit 520 and wave conditioning circuit 530 converts the DC power signals 516 and 518 to an N number of phase-shifted sinusoidal power signals 524. The number N can be equal to the number of non-ground electrodes embedded in disc 210 or a number of electrode pairs, such as the electrode pairs shown in FIG. 7A. The phase shifting circuit 520 can include N number of inverters, such that each inverter generates a square wave power signal with a different phase. The N number of phase-shifted square wave power signals 522 are conditioned by the waveform conditioning circuit 560 to generate phase-shifted sine waves 524.

The microprocessor 540 receives the operator input 320 specifying the desired shape and/or intensity of the electric field. Based on the operator input 320, the microprocessor 540 determines the appropriate phase difference between the power signals 522 to achieve the desired shape and/or intensity and, if need, the appropriate frequency and/or magnitude. The phase, frequency, and/or magnitude needed to generate the desired shape and/or intensity is stored, for example, in a lookup table. The microprocessor 540 provides the determined frequency, magnitude, and/or phase of the power signals 522 to the multi-phase synchronous modulation controller circuit 550.

The microprocessor 540 also provides control signals to the multi-inverter control circuit 560. These control signals are used to control the multi-inverter circuit for safety reasons. For example, if the temperature at the tissue treatment surface 225 exceeds a threshold, the microprocessor 540 can send signals to the multi inverter controller circuit 530 to reduce the magnitude of the power signals 522, otherwise adjust the characteristics of the power signals 522, or shutdown the inverter controller circuit 560.

Feedback from the waveform conditioning circuit 530 or, alternatively, the phase shifting circuit 520 in embodiments where the RF power generator 310 does not include the waveform conditioning circuit 560, is provided to the multi-phase synchronous modulation controller circuit 550.

The multi-phase synchronous modulation controller circuit 550 implements a feedback loop based on the needed frequency, magnitude, and/or phase of the power signals 522 received from the microprocessor 540 and the feedback from the waveform conditioning circuit 530 to correct any inaccuracy of the frequency, magnitude, and/or phase of the power signals 522. The multi-phase synchronous modulation controller circuit 550 outputs one or more signals to the multi inverter controller circuit 560 to control the frequency, magnitude, and/or phase of the power signals 522.

The multi inverter controller circuit 560 generates gating signals that are forwarded to the phase shifting circuit 520 for generation of the phase-shifted power signals 522 based on the frequency, magnitude, and/or phase of the power signals 522 received from the multi-phase synchronous modulation controller circuit 550, and the control signals received from the microprocessor 540.

Figure 6:
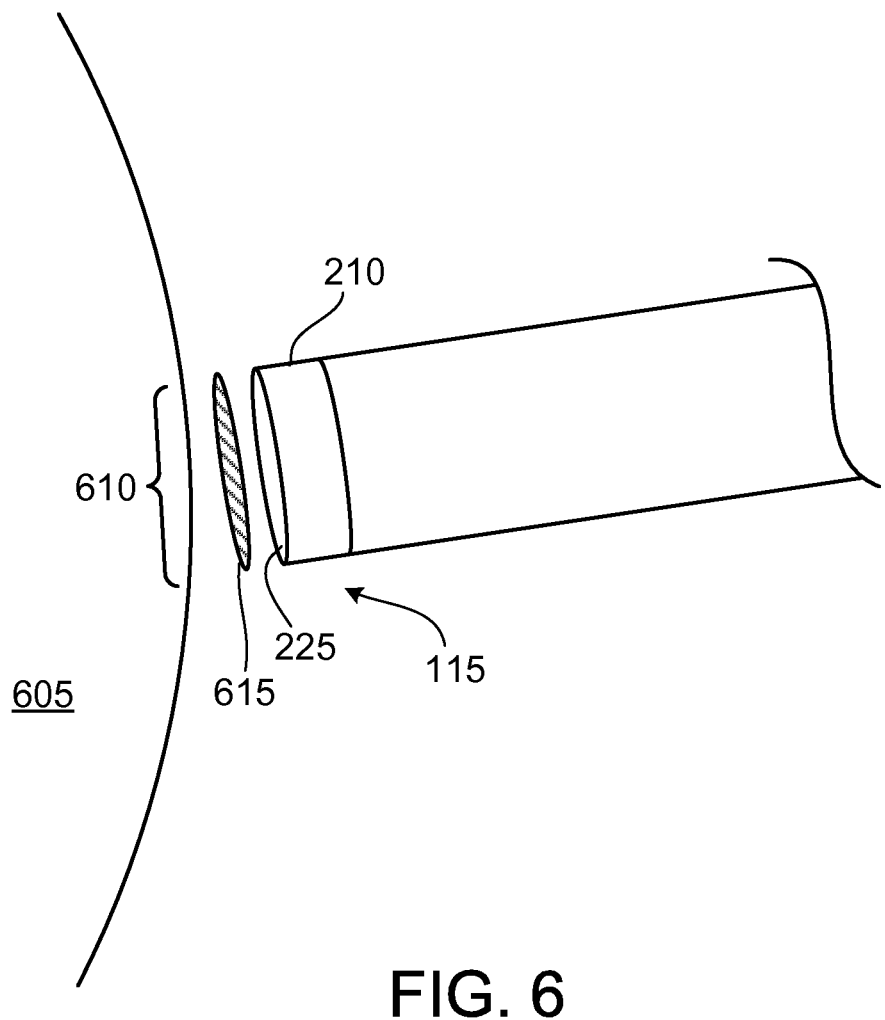
FIG. 6 is a side view showing a use of the multi-polar RF energy electrosurgical device.

Referring to FIG. 6, the electrosurgical device 100 is in use to treat body tissue 605, such as, for example, articular cartilage. Tissue treatment surface 225 is placed in contact with a tissue treatment site 610 or near enough to the tissue treatment site 610 that the electric field or plasma discharge region affects the treatment site 610. Once an operator specifies a desired shape and/or intensity of the electric field, the RF power generator 310 generates corresponding RF signals that are applied to electrodes 230a to 230e to generate an electric field, such as the electric fields of FIGS. 4A and 4B. In a treatment including, for example, ablation of tissue at tissue treatment site 610, the RF signals applied to electrodes 230a to 230e are such that a plasma 615 is formed at tissue treatment surface 225. To ablate an area of tissue, distal portion 115 along with plasma 615 is moved along the desired ablation area of tissue.

Other surgical procedures (for example, coagulation or treatment of skin lesions) are performed without forming a plasma. Rather, the electric field distributed across and extending from tissue treatment surface 225, and/or any thermal energy resulting from the electric field, is used to treat the treatment site 610. The heat is dissipated in the treated tissue limiting any collateral damage to the surrounding tissue.

Figure 7A:
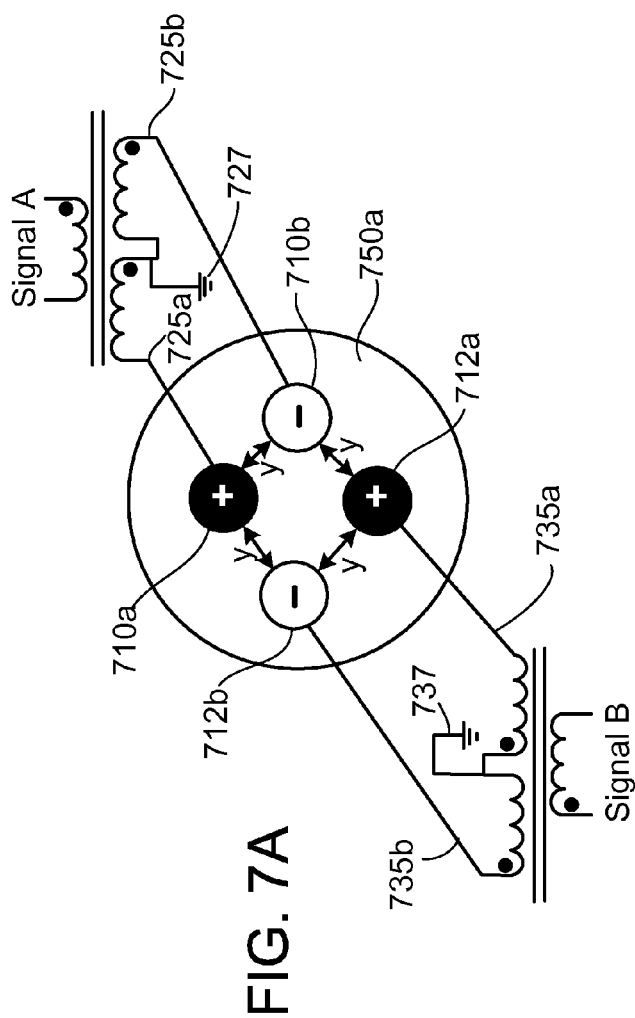
FIG. 7A is a schematic showing an alternative configuration of the electrodes and signals of the electrosurgical device.

Referring to FIG. 7A, a schematic showing an alternative configuration of the electrodes and signals of the electrosurgical device is illustrated. In this embodiment, electrodes 710a, 710b, 712a, and 712b are embedded within disc 750a and are exposed at the tissue treatment surface 225, such that the material of disc 750a does not cover the electrodes 710a, 710b, 712a, and 712b. Electrodes 710a, 710b, 712a, and 712b are adjacent to one another. Each pair of electrodes 710a and 710b, and electrodes 712a and 712b, are separated by a distance y. Electrodes 710a and 712b, and electrodes 710b and 712a, may also be separated by the distance y or by a different distance.

Figure 7B:
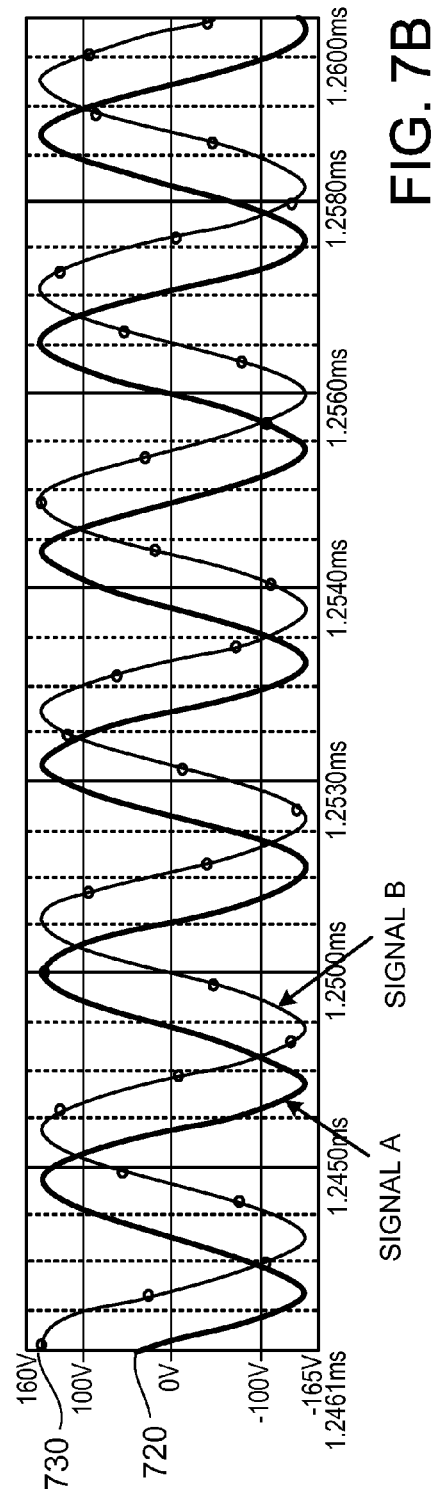
FIG. 7B is a diagram showing an example of RF signals generated by a RF power generator.

A grounding pad is attached to the patient's body, and electrodes 710a and 710b are driven by signal A and electrodes 712a and 712b are driven by signal B. As illustrated in FIG. 7B, for example, signal A 720 and signal B 730 have equal voltage magnitudes, but are out of phase (for example, 90 degrees out of phase). Signal A 720 and signal B 730 are supplied by an RF power generator.

Signal A is transformed into two input signals 725a and 725b, which are applied to electrodes 710a and 710b, respectively. Signal 725a is 180 degrees out of phase from signal 725b. As FIG. 7A illustrates, the dark circle depicting the phase of signal 725a is closest to the ground terminal 727 and the dark signal depicting the phase of signal 725b is farthest from the ground terminal 727.

Similarly, signal B is also transformed into two signals 735a and 735b that are 180 degrees out of phase and applied to electrodes 712a and 712b, respectively. Ground terminals 727 and 737 are connected to a ground pad applied to body tissue or a ground within the RF power supply. No current is applied to the ground terminals, as each pair of signals 725a and 725b, and signals 735a and 735b, are 180 degrees out of phase, thereby canceling out any current from one of the electrodes.

The electric field intensity profile extending from disc 750a can be controlled by adjusting the phases between signals 725a, 725b and 735a, 735b (adjusting the phases between signal A and signal B), as described above. For example, if phases between signals 725a 725b, and 735a, 735b are adjusted to be 90 degrees out of phase, the intensity of the electric field extending from disc 750a will be substantially uniform across disc 750a. The electric field intensity profile extending from disc 750a will change (for example, be more narrow) if signals 725a, 725b, and 735a, 735b are not equally out of phase.

Figure 7C:
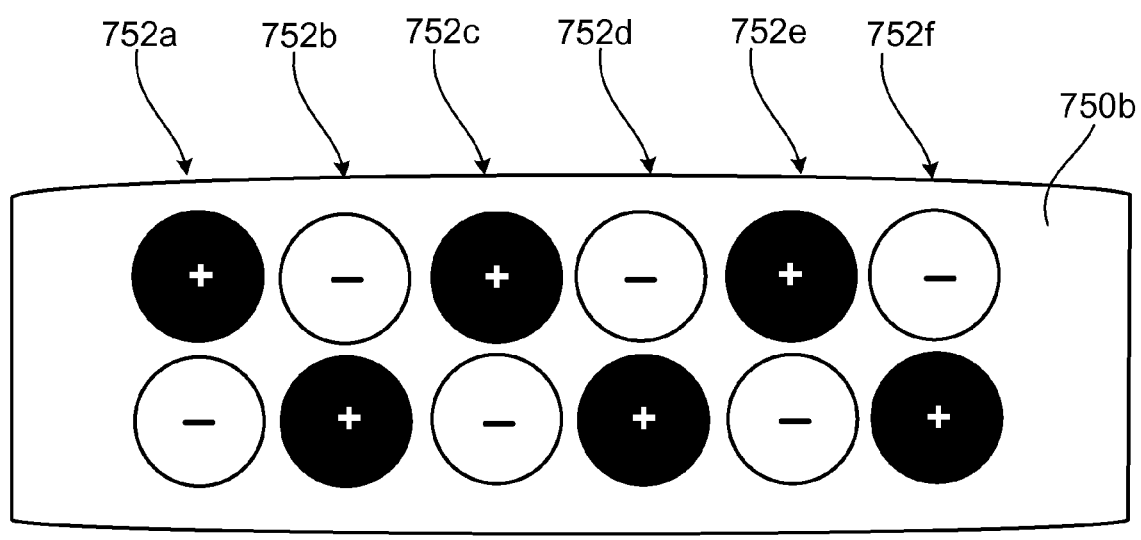
FIG. 7C is a top view of the distal portion of the electrosurgical device including six electrode pairs.

Referring to FIG. 7C, an alternative electrode layout of a disc is illustrated. In this example, disc 750b includes six electrode pairs. Each electrode pair may be driven by a distinct drive signal or more than one electrode pair may be driven by the same drive signal. An increased number of electrode pairs allows for additional electric field shapes and/or intensities to be generated.

The alternative embodiment illustrated in FIGS. 7A-7C can result in reduced voltage potentials between the electrodes in the discs 750a and 750b and the body tissue. In addition, common mode current due to capacitive coupling between the external ground and the patient's body is reduced. In particular, because of the symmetrical signal pairs 725a and 725b, and 735a and 735b, the capacitive current cancels. In general, capacitive coupling increases as the frequency of the applied RF signal increases, resulting in increased common mode currents, which can result in burns or other tissue damage. By using symmetrical signal pairs to cancel the common mode current, RF signals with higher frequencies can be used. For example, frequencies of 2 MHz, 4 MHZ, and 13.56 MHz may be used without significant common mode current resulting from capacitive coupling. These frequencies are standard FCC frequencies for which off-the-shelf RF power generators have already been created. Therefore, use of these off-the-shelf RF power generators may be used to reduce the cost of manufacturing.

Figure 7D:
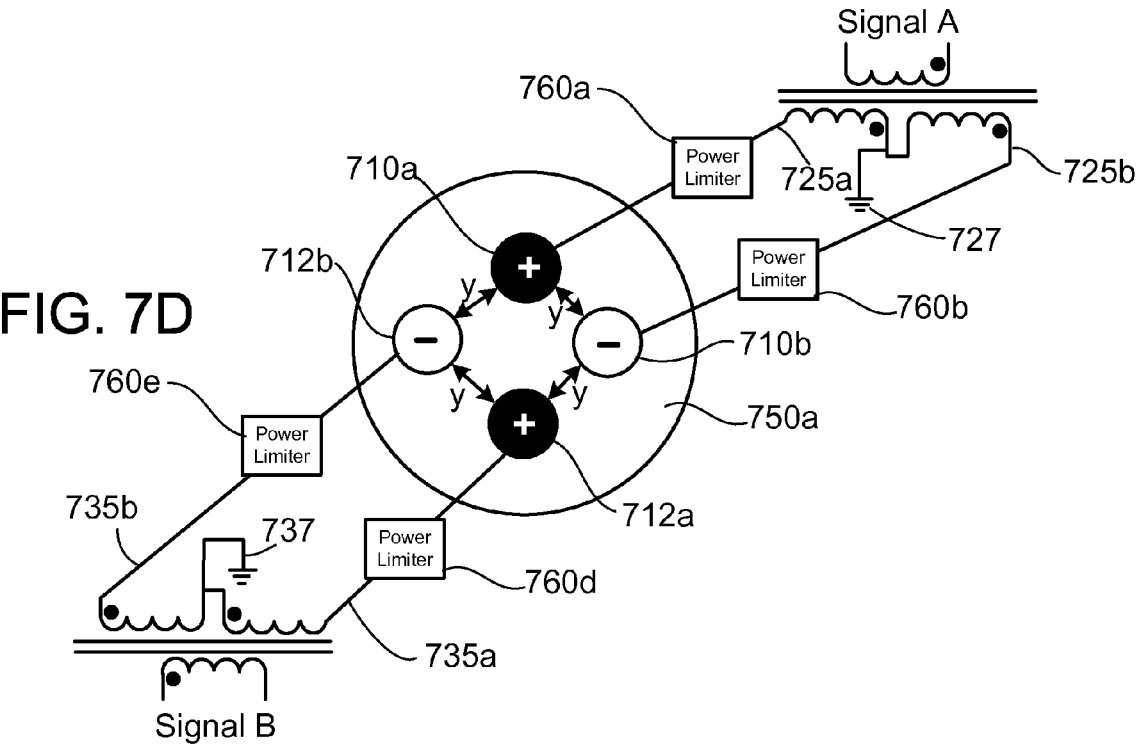
FIG. 7D is a schematic showing an alternative configuration of the electrodes and signals that includes power limiters.

FIG. 7D is a schematic showing an alternative configuration of the electrodes and signals that includes power limiters 760a-760d. This embodiment is the same as that shown in FIG. 7A, except that the input signals to electrodes 710a, 710b, 712a, and 712b. In particular, input signals 725a and 725b are applied to electrodes 710a and 710b, respective, through respective power limiters 760a and 760b. Likewise, input signals 735a and 735b are applied to electrodes 712a and 712b, respective, through respective power limiters 760d and 760e.

By limiting the power below the level provided by the input signals, the power limiters 760a, 760b, 760c, and 760d operate to insure that substantially the same power is delivered to each of electrodes 710a, 710b, 712a, and 712b. In other words, the input signals may be designed to provide more power than needed for the treatment, with the power limiters 760a, 760b, 760c, and 760d reducing the power down to the amount needed for the treatment, thereby resulting in each electrode 710a, 710b, 712a, and 712b receiving the same power. Delivering substantially the same power to each electrode may by useful in some circumstances. For example, if a plasma is generated to perform ablation, the plasma may form more closely around one of the electrodes if substantially the same power is not provided to each electrode, rather than being more evenly distributed across the electrodes.

Figure 7E:
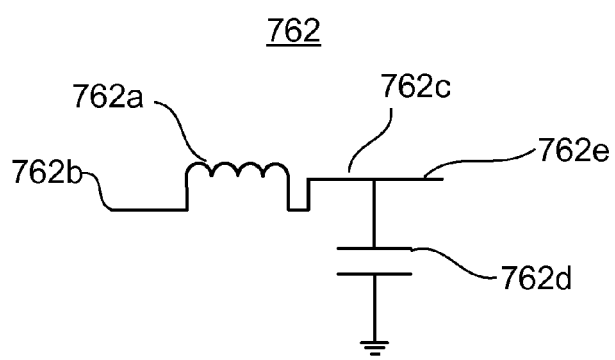
FIG. 7E is a schematic showing an example of a power limiter.

FIG. 7E shows an example of an implementation of a power limiter 762, which may be used to implement one or all of the power limiters 760a, 760b, 760c, and 760d. The power limiter 762 includes an inductor 762a that includes a first terminal 762b that can receive the input signal and a second terminal 762c that is coupled to a capacitor 762d at a first terminal of the capacitor 762d. The other terminal of the capacitor 762d is coupled to ground. The output 762e of the power limiter 762 is coupled to the second terminal 762c of the inductor 762a.

Rather than use power limiters, other implementations may use different sources of power, voltage, and/or current for each of the electrodes 710a, 710b, 712a, and 712b. Doing so may allow the phases and/or amplitude of each input signal to be changed independently.

Referring to FIGS. 8A to 8C, alternative electrode layouts including different numbers of electrodes and different electrode shapes may be included in discs 850a-c. FIG. 8A illustrates disc 850a including electrodes 802a to 802h and 804. The shape of electrodes 802a to 802h and 804 is substantially the same as those of electrodes 230a to 230e. However, the diameter of electrodes 802a to 802h and 804 may be smaller if disc 850a is substantially the same size as disc 210. Electrodes 802a to 802h may be equally separated from electrode 804 by a distance d, and equally separated from one another by a distance x, both of which, for example, may be between 1 to 10 millimeters. Electrodes 802a to 802h may be connected to a different RF signal terminal of an RF power generator. Electrode 804 may be connected to a ground. In another embodiment, any one of the electrodes 802a to 802h may be connected to a ground and electrode 804 may be connected to an RF signal terminal of the RF power generator. In some embodiments, adjacent electrodes, such as electrodes 802a and 802b may constitute a pair of electrodes. In other embodiments, opposing electrodes, such as electrodes 802a and 802e may constitute a pair of electrodes.

FIG. 8B illustrates disc 850b including electrodes 812a, 812b, and 814. Electrodes 812a, 812b, and 814 have substantially the same shape and are concentric. Electrodes 812a and 812b may be connected to a different RF signal terminal of an RF power generator. Electrode 814 may be connected to a ground. In another embodiment, any one of the electrodes 812a and 812b may be connected to a ground and electrode 814 may be connected to an RF signal terminal of the RF power generator.

FIG. 8C illustrates disc 850c including electrodes 822a to 822d and 824. Like the shape of disc 850c, the shape of electrodes 822a to 822d and 824 may be substantially rectangular. Electrodes 822a to 822d and 824 may be equally separated from one another. Electrodes 822a to 822d may be connected to a different RF signal terminal of an RF power generator. Electrode 824 may be connected to a ground. In another embodiment, any one of the electrodes 822a to 822d may be connected to a ground and electrode 824 may be connected to an RF signal terminal of the RF power generator. In some embodiments, adjacent electrodes, such as electrodes 822a and 822b may constitute a pair of electrodes. In other embodiments, opposing electrodes, such as electrodes 822a and 822d may constitute a pair of electrodes.

Moreover, electrosurgical device 100 can have other configurations. For example, electrosurgical device 100 can be provided with an internal RF generator, with power cable 120 and connector 125 connecting the internal RF generator to AC or DC power. Alternatively, in addition to an internal RF generator, electrosurgical device can include an internal battery to power the RF generator. In this case, power cable 120 and connector 125 may be eliminated.

Also, in other configurations, the phase shifting circuit 520 may include a single inverter and one or more delay elements to generate the phase shifted signals, rather than including N number of inverters. The waveform conditioning circuit 530 may include a high pass filter to remove high frequency noise from the N number of phase-shifted sinusoidal power signals 522.

In some embodiments, the RF power generator 310 does not include the waveform conditioning circuit 530 and, thus, the N number of phase-shifted square wave power signals 522 would be directly provided to the electrodes 230a to 230e exposed at the tissue treatment surface 225.

While an electrosurgical device has been described as dimensioned for endoscopic or arthroscopic surgeries, other implementations are dimensioned larger or smaller, depending on the particular application intended. In such applications, the thickness and size of the disc 210 is adjusted accordingly.

Accordingly, other embodiments are within the scope of the following claims.

What is claimed is:

1. An electrosurgical device comprising
   a plurality of electrode pairs arranged to form a tissue treatment surface, each of the electrode pairs having diametrically opposed phases based on a drive signal corresponding to the electrode pair;
   an RF power generator configured to deliver the drive signal to each electrode pair, the drive signal defining the diametrically opposed phases;
   a waveform conditioning circuit configured to define a phase of each of the drive signals, the defined phase of each of the drive signals different than a defined phase of other drive signals corresponding to other electrode pairs;
   the plurality of electrode pairs resulting in an electric field extending from the tissue treatment surface, the electric field having aspects conducive to tissue treatment of the tissue treatment surface; and
   the waveform conditioning circuit responsive to a user input for adjusting the phase of at least one of the drive signals such that an aspect of the electric field extending from the tissue treatment surface changes, each electrode of the electrode pairs maintaining the diametrically opposed phase with respect to the other electrode of the electrode pair.

2. The electrosurgical device of claim 1 wherein each of the diametrically opposed electrode pairs has a first electrode 180 degrees out of phase from a second electrode of the electrode pair.

3. The electrosurgical device of claim 1 wherein the aspect of the electrical field is a shape of the electrical field, the shape based on the defined phase of each of the drive signals.

4. The electrosurgical device of claim 1 wherein the aspect of the electrical field is an intensity of the electrical field.

5. The electrosurgical device of claim 1 wherein the power supply is configured to deliver the drive signals such that a plasma is formed in front of the tissue treatment surface.

6. The electrosurgical device of claim 1 further comprising at least one electrode coupled to ground.

7. The electrosurgical device of claim 6 wherein the ground electrode comprises a ground pad coupled to ground and configured to be coupled to a patient's body during use.

8. The electrosurgical device of claim 1 wherein the drive signals are RF drive signals with a frequency greater than 3 MHz.

9. The electrosurgical device of claim 1 wherein each of the drive signals are offset by an equal amount from the other drive signals such that each pair of electrodes is out of phase by the same degree as the other electrode pairs.

10. The electrosurgical device of claim 9 wherein the plurality of drive signals is two and each drive signal is offset 180 degrees from the other drive signal.

11. A method of performing electrosurgery with an electrosurgical device comprising:
    arranging a plurality of electrode pairs to form a tissue treatment surface on the electrosurgical device, each of the electrode pairs having diametrically opposed phases based on a drive signal corresponding to the electrode pair;

connecting, to each of the electrode pairs, an RF power generator configured to deliver the drive signal to each electrode pair, the drive signal defining the diametrically opposed phases;

defining a phase of each of the drive signals, the defined phase of each of the drive signals different than a defined phase of other drive signals corresponding to other electrode pairs such that the plurality of electrode pairs results in an electric field extending from the tissue treatment surface, the electric field having aspects conducive to tissue treatment of the tissue treatment surface; and receiving a user input for adjusting the phase of at least one of the drive signals such that an aspect of the electric field extending from the tissue treatment surface changes, each electrode of the electrode pairs maintaining the diametrically opposed phase with respect to the other electrode of the electrode pair.

12. The method of claim 11 wherein each of the diametrically opposed electrode pairs has a first electrode 180 degrees out of phase from a second electrode of the electrode pair.

13. The method of claim 11 wherein the aspect of the electrical field is a shape of the electrical field, the shape based on the defined phase of each of the drive signals.

14. The method of claim 11 wherein the aspect of the electrical field is an intensity of the electrical field.

15. The method of claim 11 further comprising delivering the drive signals such that a plasma is formed in front of the tissue treatment surface.

16. The method of claim 11 wherein arranging the electrodes further includes arranging at least one electrode coupled to ground.

17. The method of claim 16 wherein the ground electrode comprises a ground pad coupled to ground and configured to be coupled to a patient's body during use.

18. The method of claim 11 further comprising delivering the first drive signal and the second drive signal are RF drive signals with a frequency greater than 3 MHz.

19. The method of claim 11 wherein each of the drive signals are offset by an equal amount from the other drive signals such that each pair of electrodes is out of phase by the same degree as the other electrode pairs.

20. The method of claim 11 wherein the plurality of drive signals is two and each drive signal is offset 180 degrees from the other drive signal.

* * * * *